(12) United States Patent
Itou et al.

(10) Patent No.: US 10,729,661 B2
(45) Date of Patent: Aug. 4, 2020

(54) PREPARATION

(71) Applicant: SEKISUI CHEMICAL CO., LTD., Osaka, Osaka (JP)

(72) Inventors: Kazushi Itou, Osaka (JP); Takayuki Akamine, Osaka (JP); Saori Tone, Osaka (JP); Daichi Kawamura, Osaka (JP); Yoshiko Abe, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/532,840

(22) PCT Filed: Dec. 17, 2015

(86) PCT No.: PCT/JP2015/085382
§ 371 (c)(1),
(2) Date: Jun. 2, 2017

(87) PCT Pub. No.: WO2016/098857
PCT Pub. Date: Jun. 23, 2016

(65) Prior Publication Data
US 2017/0354614 A1 Dec. 14, 2017

(30) Foreign Application Priority Data

Dec. 19, 2014 (JP) .................................. 2014-258106
Jun. 29, 2015 (JP) .................................. 2015-130490

(51) Int. Cl.
*A61K 31/13* (2006.01)
*A61K 45/00* (2006.01)
*A61K 9/51* (2006.01)

(52) U.S. Cl.
CPC .......... *A61K 9/5161* (2013.01); *A61K 9/5123* (2013.01); *A61K 9/5192* (2013.01); *A61K 31/13* (2013.01); *A61K 45/00* (2013.01)

(58) Field of Classification Search
None
See application file for complete search history.

(56) References Cited

U.S. PATENT DOCUMENTS

2009/0238846 A1* 9/2009 Fujii ................... A61K 9/0014 424/400
2011/0021592 A1 1/2011 Magdassi et al.
2011/0065781 A1 3/2011 Sugimoto et al.
2011/0274731 A1 11/2011 Miyahara et al.

FOREIGN PATENT DOCUMENTS

| CN | 101352432 A | 1/2009 |
|---|---|---|
| CN | 101626754 A | 1/2010 |
| CN | 101945654 A | 1/2011 |
| CN | 102281858 A | 12/2011 |
| CN | 102985080 A | 3/2013 |
| CN | 103249406 A | 8/2013 |
| EP | 0 753 311 A1 | 1/1997 |
| EP | 2 241 314 A1 | 10/2010 |
| JP | 2006-199589 A | 8/2006 |
| JP | 2003-84293 A | 4/2009 |
| JP | 2011-20963 A | 2/2011 |
| JP | 2011-241147 A | 12/2011 |
| WO | WO-99/27918 A1 | 6/1999 |
| WO | WO-2006/025583 A1 | 3/2006 |
| WO | WO-2008/100044 A1 | 8/2008 |
| WO | WO-2010/023908 A1 | 3/2010 |
| WO | WO-2011/128623 A2 | 10/2011 |
| WO | WO-2012/045994 A1 | 4/2012 |

OTHER PUBLICATIONS

Written Opinion of the International Searching Authority (PCT/ISA/237) for Application No. PCT/JP2015/085382 dated Feb. 9, 2016 (English Translation mailed Jun. 29, 2017).
International Search Report for the Application No. PCT/JP2015/085382 dated Feb. 9, 2016.
Written Opinion of the International Searching Authority (PCT/ISA/237) for Application No. PCT/JP2015/085382 dated Feb. 9, 2016.
Piao, Hongyu et al., "A Novel Solid-in-oil Nanosuspension for Transdermal Delivery of Diclofenac Sodium", Pharmaceutical Research, 2008, vol. 25, No. 4, pp. 896-901.
Supplementary European Search Report for the Application No. EP 16 870 059.1 dated Apr. 30, 2018.
European Office Action for the Application No. 15 870 059.1 dated Sep. 6, 2019.
The First Office Action for the Application No. 201580032834.3 from The State Intellectual Property Office of the People's Republic of China dated Sep. 4, 2019.

* cited by examiner

*Primary Examiner* — Alton N Pryor
(74) *Attorney, Agent, or Firm* — Cheng Law Group, PLLC

(57) ABSTRACT

A particle comprising a first fraction containing an active ingredient and a second fraction containing a surfactant, and having a number average particle diameter of from 1 to 100 nm.

4 Claims, 2 Drawing Sheets

PREPARATION

TECHNICAL FIELD

The present invention relates to an active ingredient-containing particle, a preparation containing the active ingredient-containing particle, or the like.

BACKGROUND ART

There is used an external medicine which exerts a systemic action (a systematically acting external medicine) by entering a drug absorbed through the skin or the like into systemic circulation, or alternatively an external medicine which exerts a medicinal effect topically (a topically acting external medicine) with a drug absorbed through skin or the like. Furthermore, a cosmetic whose active ingredient is intended to be absorbed percutaneously (a percutaneous absorption cosmetic) is also used. A main technical problem in the above preparations is how to allow an active ingredient to be absorbed efficiently into the body.

A core-shell structured particle, which has a structure of covering a core portion containing an active ingredient with a shell portion containing a surfactant, is proposed as a preparation which allows an active ingredient to penetrate percutaneously (Patent Documents 1 and 2).

PRIOR ART DOCUMENT

Patent Documents

Patent Document 1: JP 2009-84293 A
Patent Document 2: WO 2006/025583 A

SUMMARY OF THE INVENTION

Problem to be Solved by the Invention

When an external medicine, such as a percutaneously absorbable preparation, which is originally required to have absorbability into the body, is designed to have an improvement in absorbability into the body, a high medicinal effect is exerted immediately after the beginning of administration. However, a main drug is absorbed at an early stage, and thus the main drug in a preparation is exhausted, which leads to a problem that a medical effect cannot be sustained. Furthermore, it is another problem that a blood level of the drug reaches, exceeding a therapeutically effective level, an adverse effect level.

Thus, an external medicine, such as a percutaneously absorbable preparation, has been required to have both absorbability into the body and sustainability. Further, an external medicine is required to have storage stability, as a generally required property, of a particle containing an active ingredient.

Further, the present inventors have found that a previously reported core-shell structured particle for an external medicine does not have a sufficient durability, and thus have a problem of disintegration in a formulation process. Specific problems proved to occur are provided below. For example, a core-shell structure is disintegrated upon contact with a solvent for preparing a liquid preparation or upon heat treatment in a coating process for production, and then an active ingredient of the core portion is deposited, crystallized, or eluted.

In connection with the above, an object of the present invention is to provide an active ingredient-containing particle which have both absorbability into the body and sustainability, and even have superior shape retainability (storage stability, and also durability such as solvent resistance and heat resistance).

Means for Solving the Problem

The present inventors have conducted diligent studies to solve the problems mentioned above, and have found that the problems mentioned above can be solved with a particle, which includes a first fraction containing an active ingredient and a second fraction containing a surfactant, and have a number average particle diameter of from 1 to 100 nm. The present invention has been accomplished by further trial-and-error based on the findings. The present invention includes the following aspects.

Aspect 1. A particle comprising a first fraction containing an active ingredient and a second fraction containing a surfactant, and having a number average particle diameter of from 1 to 100 nm.

Aspect 2. The particle according to aspect 1, wherein a portion of a surface of or a whole surface of the first fraction is coated with the second fraction.

Aspect 3, The particle according to aspect 1 or 2, wherein the number average particle diameter is from 1 nm to 20 nm.

Aspect 4. The particle according to any one of aspects 1 to 3, having a water content of 20% by weight or less.

Aspect 5. A preparation comprising the particle according to any one of aspects 1 to 4.

Aspect 6. The preparation according to aspect 5, having a water content of 20% by weight or less.

Aspect 7. The preparation according to aspect 5 or 6, wherein a weight ratio of the active ingredient to the surfactant is 1:10 to 1:50.

Aspect 8. An external medicine comprising the preparation according to any one of aspects 5 to 7.

Aspect 9. A cosmetic comprising the preparation according to any one of aspects 5 to 7.

Aspect 10. A method for producing a particle comprising a first fraction containing an active ingredient and a second fraction containing a surfactant, the method comprising a step of heat-treating a W/O emulsion containing an active ingredient in an aqueous phase and/or a dried substance of the W/O emulsion.

Aspect 11. The method for production according to aspect 10, wherein the particle has a number average particle diameter of from 1 nm to 20 nm.

Aspect 12. The method for production according to aspect 10 or 11, wherein the particle has a water content of 20% by weight or less.

Effect of the Invention

The present invention can provide an active ingredient-containing particle which have both absorbability and sustainability, and even have superior shape retainability storage stability, and also durability such as solvent resistance and heat resistance). The particle has storage stability and durability, and thus has further reduced elution of an active ingredient and even reduced crystallization of an active ingredient. Accordingly, the particle can exert superior absorbability.

MODE FOR CARRYING OUT THE INVENTION

Figure 1:
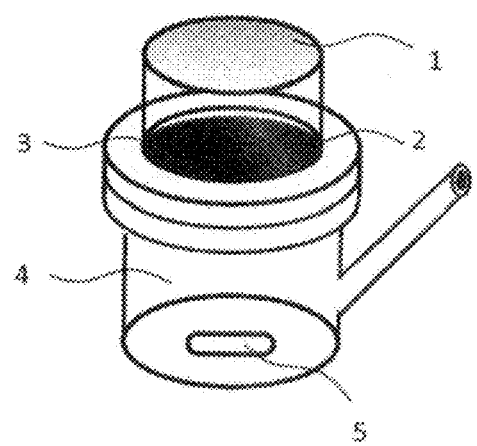
FIG. 1 is a schematic view of a cell for a test of transdermal drug-penetration used in Test Examples.
Figure 2:
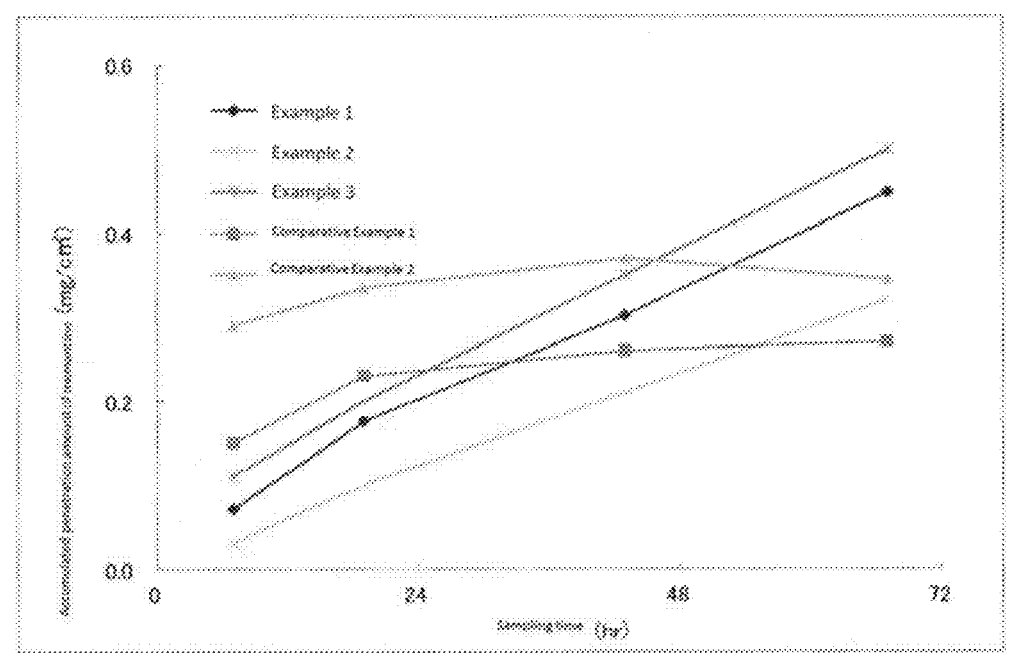
FIG. 2 is a graph showing a result of Test Example 1.
Figure 3:
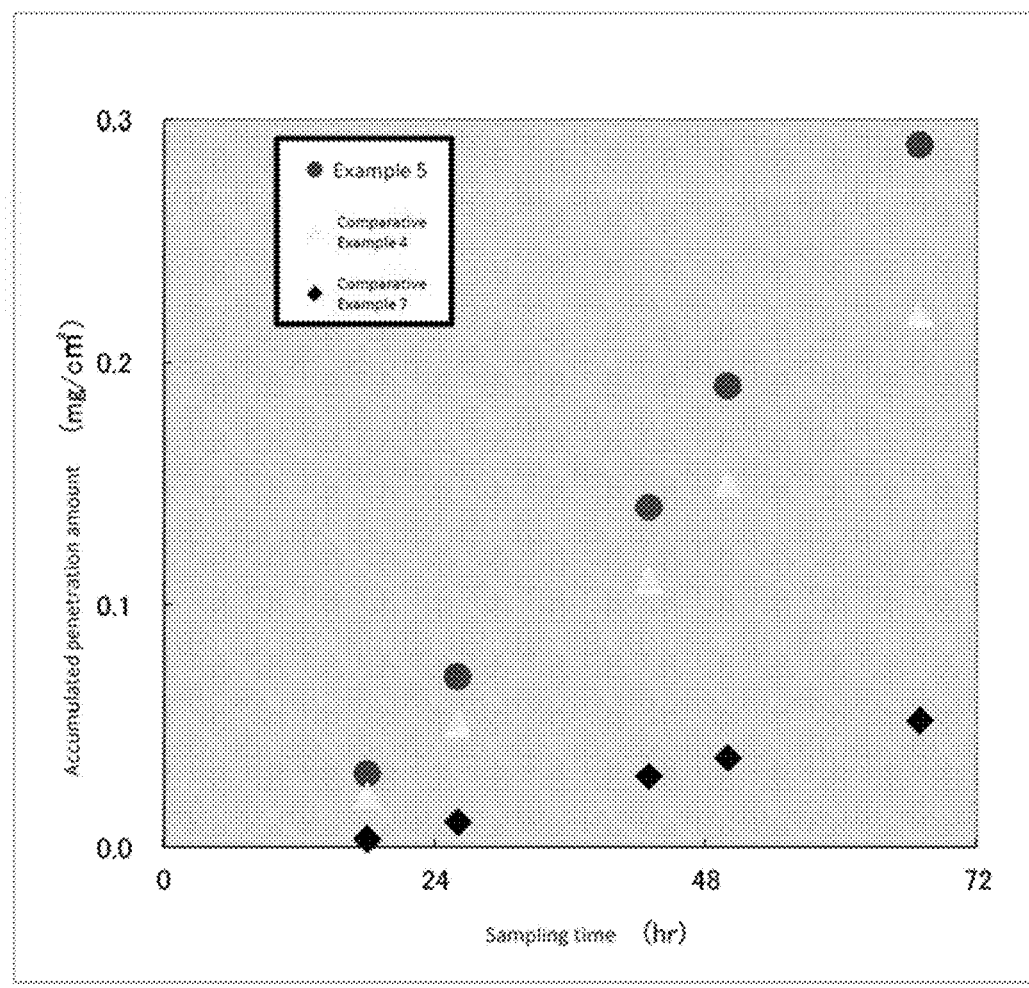
FIG. 3 is a graph showing a result of Test Example 4.

The terms "contain" and "include" as used herein encompass concepts of "consist essentially of" and "consist only of".

The term "absorbability (into the body)" as used herein encompasses concepts of, for example, "percutaneous absorbability (transdermal penetrability)", and "absorbability through routes other than the skin, such as ophthalmic, nasal, vaginal, and rectal (a suppository) routes".

1. Particle

A particle includes at least two fractions, which are a first fraction containing an active ingredient and a second fraction containing a surfactant. The first fraction and the second fraction should only be bonded (preferably by an intermolecular force) together to form an aggregate. In the particle, a portion of a surface of or a whole surface of the first fraction (for example, 30% or more, preferably 50% or more, more preferably 70% or more, further more preferably 85% or more, still more preferably 95% or more, yet more preferably 99% or more of the surface of the first fraction) is preferably, with respect to absorbability and sustained releasability of an active ingredient, coated with the second fraction. Examples of embodiments of the particle include a core-shell structured body in which the first fraction corresponds to a core portion and the second fraction corresponds to a shell portion involving the core portion.

It has been realized that the size of a particle is important to take an effect of the present invention. A number average particle diameter is required to be from 1 nm to 100 nm to take an effect of the present invention. The number average particle diameter is preferably, with respect to an effect of the present invention, from 1 to 50 nm, more preferably from 1 to 30 nm, further more preferably from 1 to 20 nm, still more preferably from 1 to 15 nm, yet more preferably from 2 nm to 10 nnm.

A shape of the particle is not particularly limited. When the particle diameter is within the range described above, the particle can have both an excellent absorbability of an active ingredient, and storage stability and durability, regardless of the shape. The shapes of the particle include, for example, spherical shape, rod shape, cubic shape, lenticular shape, and echinoid-like shape.

The number average particle diameter of the particle in the present invention refers to a calculated number average diameter of a fraction having a peak within 1 nm to 100 nm observed by dynamic light scattering of a dispersion in a solvent (e.g., squalane, and the like).

A water content of the particle is preferably 20% by weight or less, more preferably 10% by weight or less, further more preferably 5% by weight or less, still more preferably 1% by weight or less. Especially preferably, the particle contains substantially no water. That is, the particle of the present invention is different from a particle in a W/O emulsion.

1.1 First Fraction

A first fraction contains at least an active ingredient.

The active ingredient is not particularly limited, so long as it is a component having a physiological activity. Preferably, the active ingredient is a component which is formulated for the purpose of exerting its physiological activity. In a preferable embodiment, a component, which is not formulated for the purpose of exerting its physiological activity in light of an amount formulated, a method for formulation, or the like, is not involved in the active ingredient, although the component has a physiological effect. Examples of the active ingredients include components formulated in a pharmaceutical, a cosmetic, and the like as an active ingredient. Most of the active ingredients of a pharmaceutical or a cosmetic are organic substances. Thus, the active ingredient may be an organic substance.

Active ingredients that can be used, which are formulated into a pharmaceutical, include an active ingredient required to have a systemic action, and an active ingredient required to have a topical action.

Specific examples of the active ingredients formulated into a pharmaceutical include, but are not particularly limited to, an antidementia drug, an antiepileptic drug, an antidepressant, an antiparkinsonian drug, an antiallergic drug, an anticancer drug, an antidiabetic drug, an antihypertensive drug, an erectile dysfunction drug, a dermatosis drug, a local anesthetics, a peptide drug, and a pharmaceutically acceptable salt thereof. More specifically, examples thereof include memantine, donepezil, rivastigmine, galanthamine, nitroglycerin, lidocaine, fentanyl, male hormones, female hormones, nicotine, clomipramine, diphenhydramine, nalfurafine, metoprolol, fesoterodine, ldenafil, nalfurafine, tandospirone, beraprost sodium, taltirelin, lurasidone, nefazodone, rifaximin, benidipine, doxazosin, nicardipine, formoterol, lomerizine, amlodipine, vardenafil, octreotide, teriparatide, bucladesine, cromoglicic acid, Sandostatin, teriparatide, lixisenatide, exenatide, liraglutide, Lanreotide, glucagon, oxytocin, calcitonin, elcatonin, Glatiramer, and a pharmaceutically acceptable salt thereof.

The pharmaceutically acceptable salt is not particularly limited, and any of acid salts and basic salts can be employed. Examples of the acid salts include inorganic acid salts such as hydrochloride, hydrobromide, sulfate, nitrate, and phosphate; and organic acid salts such as acetate, propionate, tartrate, fumarate, maleate, malate, citrate, methanesulfonate, bensenesulfonate, and p-toluenesulfonate. Further, examples of the basic salts include salts of alkali metals such as sodium and potassium; and alkaline-earth metal salts such as a calcium salt and a magnesium, salt. Examples of the salts of the active ingredient described above include, memantine hydrochloride, donepezil hydrochloride, rivastigmine tartrate, galanthamine hydrobromide, clomipramine hydrochloride, diphenhydramine hydrochloride, nalfurafine hydrochloride, metoprolol tartrate, fesoterodine fumarate, ldenafil hydrochloride hydrate, nalfurafine hydrochloride, tandospirone citrate, beraprost sodium, lurasidone hydrochloride, nefazodone hydrochloride, benidipine hydrochloride, doxazosin mesilate, nicardipine hydrochloride, formoterol fumarate, lomerizine hydrochloride, and amlodipine besilate.

An active ingredient, to be formulated into a cosmetic is not particularly limited, so long as it is required to penetrate transdermally. Examples of the active ingredients include vitamin ingredients such as vitamin C and vitamin E; moisturizing ingredients such as hyaluronic acid, ceramide, and collagen; skin-whitening ingredients such as tranexamic acid and arbutin; hair growth ingredients such as minoxidil; beauty ingredients such as FGF (fibroblast growth factor) and EGF (epidermal growth factor); and a salt or a derivative thereof.

The active ingredient is preferably hydrophilic.

When the active ingredient is a hydrophilic drug, the active ingredient has typically, but not particularly limited to, the following properties:
a molecular weight being 10000 or less, and
an octanol-water partition coefficient being from −6 to 6.

With respect to the above, the molecular weight is preferably 5000 or less, more preferably 2000 or less, further more preferably 1000 or less. The lower limit of the molecular weight is not particularly limited, but is usually 50 or more.

The octanol-water partition coefficient is, with respect to the above, preferably from −3 to 5, more preferably from −1 to 4.

The octanol-water partition coefficient in the present invention refers to a calculated number obtained by adding a drug to a flask containing octanol and an aqueous buffer of pH 7, shaking the flask, and then performing calculation with an equation below using a drug concentration of each phase.

Octanol-water partition coefficient=$\log_{10}$ (concentration in an octanol phase/concentration in an aqueous phase)

An amount of the active ingredient contained in the particle depends on the kinds of the active ingredient, but can be, for example, from 0.1 to 30% by weight (based on a total weight of all raw materials contained in the particle) as a weight of a raw material charged.

The first fraction may contain two or more active ingredients as the active ingredient as needed.

The first fraction may further contain at least one other component in addition to the active ingredient. Examples of the other components include, but are not particularly limited to, a stabilizing agent, an absorption enhancer, a stimulation reducing agent, and an antiseptic.

The stabilizing agent has an action of stabilizing a structure of a particle, prevents unintentional early disintegration of the particle, and ensures a sustained releasing effect of the active ingredient.

Specific examples of the stabilizing agents include, but are not particularly limited to, polysaccharides, proteins, and a hydrophilic polymeric material. One kind or two or more kinds of the stabilizing agents may be contained. A content of the stabilizing agent in the first fraction can be set appropriately depending on the kinds of the stabilizing agent. The stabilizing agent can be also formulated so that, for example, a weight ratio of the active ingredient to the stabilizing agent can be from 1:0.1 to 1:10.

Specific examples of the absorption enhancers include, but are not particularly limited to, a higher alcohol, N-acyl sarcosine and its salt, a higher monocarboxylic acid, a higher monocarboxylic acid ester, an aromatic monoterpene fatty acid ester, a dicarboxylic acid having 2 to 10 carbon atoms and its salt, a polyoxyethylene alkyl ether phosphoric acid ester and its salt, lactic acid, a lactic acid ester, and citric acid. One kind or two or more kinds of the absorption enhancers may be contained. A content of the absorption enhancer in the first fraction can be set appropriately depending on the kinds of the absorption enhancer. The absorption enhancer can be also formulated so that, for example, a weight ratio of the active ingredient to the absorption enhancer can be from 1:0.01 to 1:50.

Specific examples of the stimulation reducing agents include, but are not particularly limited to, a hydroquinone glycoside, pantethine, tranexamic acid, lecithin, titanium oxide, aluminum hydroxide, sodium nitrite, sodium hydrogen nitrite, soybean lecithin, methionine, glycyrrhetinic acid, BHT, BHA, vitamin E and its derivative, vitamin C and its derivative, benzotriazole, propyl gallate, and mercaptobenzimidazole. One kind or two or more kinds of the stimulation reducing agents may be contained. A content ratio of the stimulation reducing agent in the first fraction can be set appropriately depending on the kinds of the stimulation reducing agent. The stimulation reducing agent can be also formulated so that, for example, a weight ratio can be from 0.1% by weight to 50% by weight.

Specific examples of the antiseptics include, but are not particularly limited to, methyl paraoxybenzoate, propyl paraoxybenzoate, phenoxy ethanol, and thymol. A content ratio of the antiseptic in the first fraction can be set appropriately depending on the kinds of the antiseptics. The antiseptic can be also formulated so that, for example, a weight ratio can be from 0.01% by weight to 10% by weight. One kind or two or more kinds of the antiseptics may be contained.

1.2 Second Fraction

A second fraction contains at least a surfactant.

The surfactants that can be used include a surfactant having a weighted average of HLB value of 10 or less, preferably 5 or less, more preferably 3 or less.

In the present invention, HLB (an abbreviation of Hydrophile Lypophile Balance) value, which is an index to know whether an emulsifier is hydrophilic or lipophilic, is between 0 and 20. The smaller the HLB value indicates that an emulsifier has a stronger lipophilicity. The HLB value in the present invention is calculated by the Griffin equation below.

$$HLB\ value=20\times\{(\text{molecular weight of hydrophilic portion})/(\text{total molecular weight})\}$$

A weighted average of HLB value is calculated as follows.

For example, when a weight of a surfactant raw material, which has an HLB value of h, employed for particle synthesis is x, a weight of another surfactant raw material, which has an HLB value of B, employed for particle synthesis is y, and a weight of another surfactant raw material, which has an HLB value of C, employed for particle synthesis is z, a formula for computation of a weighted average value is as follows:

$$(xA+yB+zC)/(x+y+z).$$

The surfactant has a melting point of preferably 50° C. or less, more preferably 40° C. or less, with respect to absorbability.

The surfactant is not particularly limited, but can be selected appropriately according to the purpose of use. For example, the surfactant can widely be selected from surfactants which can be used as a pharmaceutical or a cosmetic. Further, two or more surfactants can be used in combination.

The surfactant can be any of a nonionic surfactant, an anionic surfactant, a cationic surfactant, and an amphoteric surfactant.

Examples of the nonionic surfactants include, but are not particularly limited to, a fatty acid ester, a fatty alcohol ethoxylate, a polyoxyethylene alkyl phenyl ether, an alkyl glycoside, and a fatty acid alkanolamide, as well as a polyoxyethylene castor oil, and a hydrogenated castor oil.

The fatty acid ester is preferably, but is not particularly limited to, a sugar fatty acid ester. Specific examples of the fatty acid esters include esters of sucrose with fatty acids such as erucic acid, oleic acid, lauric acid, stearic acid, and behenic acid.

Examples of the other fatty acid esters include, but are not particularly limited to, esters of at least one of glycerol, polyglycerol, polyoxyethylene glycerol, sorbitan, polyoxyethylene sorbitol, and the like, with a fatty acid.

Examples of the anionic surfactants include an alkyl sulfuric acid ester salt, a polyoxyethylene alkyl ether sulfuric acid ester salt, an alkyl benzenesulfonic acid salt, a fatty acid salt, and a phosphoric acid ester salt.

Examples of the cationic surfactants include an alkyl trimethylammonium salt, a dialkyl dimethyl ammonium salt, an alkyl dimethylbenzylammonium salt, and amine salts.

Examples of the amphoteric surfactants include an alkylamino fatty acid salt, an alkyl betaine, and alkylamine oxide.

The surfactants used preferably include particularly a sucrose fatty acid ester, a glycerol fatty acid ester, a polyoxyethylene glycerol fatty acid ester, a sorbitan fatty acid ester, a polyoxyethylene sorbitol fatty acid ester, a polyoxyethylene castor oil, and a hydrogenated castor oil.

The surfactant may be, but is not particularly limited to, a surfactant having a hydrocarbon chain (such as an alkyl chain, an alkenyl chain, or an alkynyl chain). The length of the hydrocarbon chain can widely be selected, but is not particularly limited to, from 8 to 30 carbon atoms in the main chain, and particularly preferably, the length of the hydrocarbon chain is from 10 to 24.

In the case where a surfactant having a hydrocarbon chain is solely used, or a surfactant having a hydrocarbon chain and another surfactant are used in combination, when a weight ratio of the active ingredient to ail hydrocarbon chains contained in the surfactant is from 1:1 to 1:70, the particle according to the present invention has excellent sustained absorbability. In this regard, the weight ratio is preferably from 1:2 to 1:70 or 1:2 to 1:50, more preferably from 1:3 to 1:30, further more preferably from 1:5 to 1:20.

The second fraction may further contain at least one other component in addition to the surfactant. Examples of the other components include, but are not particularly limited to, a stimulation reducing agent, an analgesic, an absorption enhancer, a stabilizing agent, and an antiseptic.

Specific examples of the stimulation reducing agents include, but are not particularly limited to, a hydroquinone glycoside, pantethine, tranexamic acid, lecithin, titanium oxide, aluminum hydroxide, sodium nitrite, sodium hydrogen nitrite, soybean lecithin, methionine, glycyrrhetinic acid, BHT, BHA, vitamin E and its derivative, vitamin C and its derivative, benzotriazole, propyl gallate, and mercaptobenzimidazole. One kind or two or more kinds of the stimulation reducing agents may be contained. A content ratio of the stimulation reducing agent in the second fraction can be set appropriately depending on the kinds of the stimulation reducing agent. The stimulation reducing agent can be also formulated so that, for example, a weight ratio can be from 0.1% by weight to 50% by weight.

Specific examples of the analgesics include, but are not particularly limited to, local anesthetics, such as procaine, tetracaine, lidocaine, dibucaine, and prilocaine, and salts thereof. One kind or two or more kinds of the analgesics may be contained. A content ratio of the analgesic in the second fraction can be set appropriately depending on the kinds of the analgesic. The analgesic can be also formulated so that, for example, a weight ratio can be from 0.1% by weight to 30% by weight.

Specific examples of the absorption enhancers include, but are not particularly limited to, a higher alcohol, N-acyl sarcosine and its salt, a higher monocarboxylic acid, a higher monocarboxylic acid ester, an aromatic monoterpene fatty acid ester, a dicarboxylic acid having 2 to 10 carbon atoms and its salt, a polyoxyethylene alkyl ether phosphoric acid ester and its salt, lactic acid, a lactic acid ester, and citric acid. One kind or two or more kinds of the absorption enhancers may be contained. A content ratio of the absorption enhancer in the second fraction can be set appropriately depending on the kinds of the absorption enhancers. The absorption enhancer can be also formulated so that, for example, a weight ratio can be from 0.1% by weight to 30% by weight.

The stabilizing agent has an action of stabilizing a core-shell structure of a particle, prevents unintentional early disintegration of the core-shell structure, and ensures a sustained releasing effect of the active ingredient.

Specific examples of the stabilizing agents include, but are not particularly limited to, a fatty acid and its salt; parahydroxybenzoic acid esters, such as methylparaben and propylparaben; alcohols, such as chlorobutanol, benzyl alcohol and phenylethyl alcohol; thimerosal, acetic anhydride, sorbic acid, sodium hydrogen sulfite, L-ascorbic acid, sodium ascorbate, butylated hydroxyanisole, butylated hydroxytoluene, propyl gallate, tocopherol acetate, dl-α-tocopherol, proteins, and polysaccharides. One kind or two or more kinds of the stabilizing agents may be contained. A content of the stabilizing agent in the second fraction can be set appropriately depending on the kinds of the stabilizing agents. The stabilizing agent can be also formulated so that, for example, a weight ratio of the sucrose fatty acid ester to the stabilizing agent can be from 1:00.1 to 1:50.

Specific examples of the antiseptics include, but are not particularly limited to, methyl paraoxybenzoate, propyl paraoxybenzoate, phenoxy ethanol, and thymol. One kind or two or more kinds of the antiseptics may be contained. A content ratio of the antiseptic in the second fraction can be set appropriately depending on the kinds of the antiseptics. The antiseptic can be also formulated so that, for example, a weight ratio can be from 0.01% by weight to 10% by weight.

2. Preparation

A preparation according to the present invention contains at least the particle described above.

A content ratio of the particle in the preparation is not particularly limited. In the case of an adhesive preparation, an ointment, a cream, or a gel, the amount of the particle contained is preferably 10% by weight or more and 70% by weight or less, more preferably 20% by weight or more and 50% by weight or less.

A weight ratio between the active ingredient and the surfactant (active ingredient weight:surfactant weight) in the preparation can be set appropriately within a range where an effect of the present invention is exerted. For example, the weight ratio can be from 1:3 to 1:100. Under this condition, the preparation according to the present invention exerts an excellent absorbability. In this regard, the weight ratio is preferably from 1:5 to 1:100, more preferably from 1:10 to 1:50 or from 1:15 to 1:50.

The preparation according to the present invention can be used for preparations, such as external medicines (e.g., an external skin medicine, eye drops, a nasal spray, a suppository, and oral cavity drugs) and cosmetics, which are intended to be absorbed transdermally or transmucosally, for wide variety of purposes of use according to the kinds of the active ingredients.

The preparation according to the present invention stays effective generally, but not particularly limited to, 1 day to 1 week. In preferable embodiment, the preparation according to the present invention is used by once-a-day to once-a-week administration.

When the preparation according to the present invention is an external medicine, a target disease differs depending on the kinds of the active ingredients.

The preparation according to the present invention is not particularly limited. The preparations can he used as an adhesive preparation (e.g., a tape (e.g., reservoir type, or matrix type) such as a piaster; a poultice; a patch; or a microneedle), anointment, an external liquid preparation (e.g., a liniment, or a lotion), a spray (e.g., an external aerosol, or a pump spray preparation; a cream, a gel, an ophthalmic solution, an eye ointment, a nasal spray, a suppository, a semisolid formulation for rectal use, or an enema formulation.

A water content of the preparation according to the present invention is preferably 20% by weight or less. More preferably, the preparation contains substantially no water. This makes it possible to improve a shape retainability of the particle. Accordingly, in combination with the intrinsic shape retainability of the particle, an elution of the active ingredient from the particle and even crystallization of the active ingredient can further be reduced. Consequently, the particle can exert superior absorbability. In this regard, the preparation according to the present invention is preferably used as a preparation, such as a plaster, a patch, an ointment, or a gel, whose water content is adjusted to 20% by weight or less (more preferably a preparation containing substantially no water).

2.1 Base Phase

The preparation according to the present invention may further contain a phase containing a base (a base phase). The base phase may contain the particle described, above. In this case, the particle is dispersed or dissolved in the base phase.

The base is not particularly limited. The base can widely be selected from bases which can be used as a pharmaceutical (particularly, an external medicine) and a cosmetic.

The base can be selected appropriately from, but not particularly limited to, bases which are suitable for dispersing or dissolving the particle in accordance with an intended use or the like.

Further, two or more bases may be used in combination.

Examples of the bases include, but are not particularly limited to, an oleaginous base, and an aqueous base. Examples of the oleaginous bases include a vegetable oil, an animal oil, a neutral lipid, a synthetic oil and fat, a sterol derivative, waxes, hydrocarbons, monoalcohol carboxylic acid esters, oxyacid esters, polyalcohol fatty acid esters, silicones, higher alcohols, higher fatty acids, and fluorine-based oils. Examples of the aqueous bases include water and a (poly)alcohol.

Examples of the vegetable oils include, but are not particularly limited to, soybean oil, sesame oil, olive oil, coconut oil, balm oil, rice oil, cottonseed oil, sunflower oil, rice-bran oil, cacao butter, corn oil, safflower oil, castor oil, and rapeseed oil.

Examples of the animal oils include, but are not particularly limited to, mink oil, turtle oil, fish oil, beef tallow, horse fat, pig fat, and shark squalane.

Examples of the neutral lipids include, but are not particularly limited to, triolein, trilinolein, trimyristin, tristearin, and triarachidonin.

Examples of the synthetic oils and fats include, but are not particularly limited to, phospholipid and azone.

Examples of the sterol derivatives include, but are not particularly limited to, dihydro cholesterol, lanosterol, dihydrolanosterol, phytosterol, cholic acid, and cholesteryl linoleate.

Examples of the waxes include candelilla wax, carnauba wax, rice wax, Japan wax, beeswax, montan wax, ozokerite, ceresin, paraffin wax, microcrystalline wax, petrolatum, Fischer-Tropsch wax, polyethylene wax, and an ethylene-propylene copolymer.

Examples of the hydrocarbons include liquid paraffin (mineral oil), heavy liquid isoparaffin, light liquid isoparaffin, an α-olefin oligomer, polyisobutene, hydrogenated polyisobutene, polybutene, squalane, olive-derived squalane, squalene, vaseline, and hard paraffin.

Examples of the monoalcohol carboxylic acid esters include octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, lanolin fatty acid octyldodecyl, hexyldecyl dimethyloctanoate, octyldodecyl erucate, hydrogenated castor oil isostearate, ethyl oleate, avocado oil fatty acid ethyl, isopropyl myristate, isopropyl palmitate, octyl palmitate, isopropyl isostearate, lanolin fatty acid, isopropyl, diethyl sebacate, diisopropyl sebacate, dioctyl sebacate, diisopropyl adipate, dibutyl octyl sebacate, diisobutyl adipate, dioctyl succinate, and triethyl citrate.

Examples of the oxyacid esters include cetyl lactate, diisostearyl malate, and hydrogenated castor oil monoisostearate.

Examples of the polyalcohol fatty acid esters include glyceryl trioctanoate, glyceryl trioleate, glyceryl triisostearate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate/eicosadioate, trimethylolpropane triethylhexanoate, trimethylolpropane triisostearate, neopentylglycol dioctanoate, neopentylglycol dicaprate, 2-butyl-2-ethyl-1,3-propanediol dioctanoate, propylene glycol dioleate, pentaerythrityl tetraoctanoate, pentaerythrityl hydrogenated rosinate, ditrimethylolpropane triethyl hexanoate, ditrimethylolpropane (isostearate/sebacate), pentaerythrityl triethyl hexanoate, dipentaerythrityl (hydroxystearate/stearate/rosinate), diglyceryl diisostearate, polyglyceryl tetraisostearate, polyglyceryl-10 nonaisostearate, polyglyceryl-8 deca(erucate/isostearate/ricinoleate), hexyldecanoic acid/sebacic acid) diglyceryl oligo ester, glycol distearate (ethylene glycol distearate), 3-methyl-1,5-pentanediol dineopentanoate, and 2,4-diethyl-1,5-pentanediol dineopentanoate.

Examples of the silicones include dimethicone (dimethylpolysiloxane); highly polymerized dimethicone (highly polymerized dimethylpolysiloxane); cyclomethicone (cyclodimethylsiloxane, decamethylcyclopentasiloxane); phenyl trimethicone; diphenyl dimethicone; phenyl dimethicone; stearoxypropyl dimethylamine; an (aminoethylaminopropyl methicone/dimethicone)copolymer; dimethiconol; a dimethiconol crosspolymer; a silicone resin; a silicone rubber; an amino-modified silicone, such as aminopropyl dimethicone or amodimethicone; a cation-modified silicone; a polyether-modified silicone, such as dimethicone copolyol; a polyglycerol-modified silicone; a sugar-modified silicone; a carboxylic acid-modified silicone; a phosphoric acid-modified silicone; a sulfuric acid-modified silicone; an alkyl-modified silicone; a fatty acid-modified silicone; an alkyl ether-modified silicone; an amino acid-modified silicone; a peptide-modified silicone; a fluorine-modified silicone; a cation-modified or polyether-modified silicone; an amino-modified or polyether-modified silicone; an alkyl-modified or polyether-modified silicone; and a polysiloxane/oxyalkylene copolymer.

Examples of the higher alcohols include cetanol, myristyl alcohol, oleyl alcohol, lauryl alcohol, cetostearyl alcohol, stearyl alcohol, arachidyl alcohol, behenyl alcohol, jojoba alcohol, chimyl alcohol, selachyl alcohol, batyl alcohol, hexyldecanol, isostearyl alcohol, 2-octyldodecanol, and dimer diol.

Examples of the higher fatty acids include lauric acid, myristic acid, palmitic acid, stearic acid, isostearic acid, behenic acid, undecylenic acid, 12-hydroxystearic acid, palmitoleic acid, oleic acid, linoleic acid, linoleinic acid, erucic acid, docosahexaenoic acid, eicosapentaenoic acid, isohexadecanoic acid, anteisoheneicosanoic acid, long-chain branched fatty acid, dimer acid, and hydrogenated dimer acid.

Examples of the fluorine-based oils include perfluorodecane, perfluorooctane, and perfluoropolyether.

Examples of the (poly)alcohols include ethanol, isopropanol, glycerol, propylene glycol, 1,3-butylene glycol, and polyethylene glycol.

Furthermore, examples of the other bases include, but are not particularly limited to, bases used for an adhesive preparation (e.g., a tape (e.g., reservoir type, or matrix type) such as a plaster; a poultice; a patch; or a microneedle), an ointment, an external liquid preparation (e.g., a liniment, or a lotion), a spray (e.g., an external aerosol, or a pump spray preparation; a cream, a gel, an ophthalmic solution, an eye ointment, a nasal spray, a suppository, a semisolid formulation for rectal use, or an enema formulation.

2.2 Other Additive Component

The preparation according to the present invention may contain other additive components in accordance with its form, intended use, or the like.

examples of the additive components include, but are not particularly limited to, a diluent, a colorant, a lubricant, a binder, an emulsifier, a thickener, a wetting agent, a stabilizer, a preservative, a solvent, a solubilizing agent, a suspending agent, a buffer, a pH adjuster, a gelling agent, an adhesive agent, an antioxidant, an absorption enhancer, a stimulation alleviating agent, an antiseptic, a chelator, and a dispersant.

In the preparation according to the present invention, when the preparation does not contain the base phase described above, the particle may further be dispersed in other component. Further, when the preparation contains the base phase described above, the base phase in which the particle is contained (hereinafter, may also be generally called as "particle-containing fundamental material") may further be dispersed in other component. In this case, the preparation according to the present invention is provided by, for example, dispersing under mixing or emulsifying the particle or the particle-containing fundamental material in a component, which cannot completely dissolve the particle or the particle-containing fundamental material. The component can be selected appropriately in accordance with dosage forms, and is not particularly limited. For example, in order to provide the preparation as an adhesive preparation (e.g., a tape (e.g., reservoir type, or matrix type), such as a plaster, or a hard salve; a poultice; a patch; or a microneedle), an ointment, an external liquid preparation (e.g., a liniment, or a lotion), a spray (e.g., an external aerosol, or a pump spray preparation; a cream, a gel, an ophthalmic solution, an eye ointment, a nasal spray, a suppository, a semisolid formulation for rectal use, an enema formulation, or the like, the particle or the particle-containing fundamental material can be dispersed under mixing or emulsified in a base or the like used for each of the dosage form.

3. Method for Production of a Particle and a Preparation

The particle according to the present invention can be produced by, but not particularly limited to, for example, a method including a step of drying W/O emulsion containing an active ingredient in an aqueous phase.

The W/O emulsion is not particularly limited, so long as it is a so-called water in oil emulsion, and specifically it is an emulsion in which droplets of an aqueous solvent are dispersed in an oil solvent.

The W/O emulsion containing an active ingredient in an aqueous phase can be obtained by, for example, mixing an aqueous solvent (e.g., water or a buffer aqueous solution) containing an active ingredient, and an oil solvent (e.g., cyclohexane, hexane, or toluene) containing a surfactant. The aqueous solvent containing an active ingredient may further contain an additive component, such as a stabilizing agent, an absorption enhancer, or a stimulation reducing agent, as needed, in addition to the active ingredient. The oil solvent containing a surfactant may further contain an additive component, such as a stimulation reducing agent, an analgesic, an absorption enhancer, or a stabilizing agent, as needed, in addition to an active ingredient. A method for the mixing is not particularly limited, so long as it can produce a W/O emulsion. For example, the methods for the mixing include stirring with a homogenizer and the like. When stirred with a homogenizer, the stirring condition is, for example, from about 5000 to about 50000 rpm, more preferably from about 10000 to about 30000 rpm.

A weight ratio between the active ingredient and the surfactant (active ingredient weight:surfactant weight) in the above W/O emulsion is not particularly limited, so long as a particle according to the present invention having a number average particle diameter of from 1 to 100 nm can finally be obtained. The weight ratio between the active ingredient and the surfactant is, for example, 1:3 to 1:100, preferably 1:5 to 1:70, more preferably 1:10 to 1:50.

A method for drying the W/O emulsion including an active ingredient in an aqueous phase is not particularly limited, so long as it can remove the solvent (an aqueous solvent and an oil solvent) contained in the emulsion. For example, the methods include freeze-drying, and vacuum-drying, preferably freeze-drying.

The method for drying the W/O emulsion preferably further includes a step of heat-treating the W/O emulsion containing an active ingredient in an aqueous phase, or a dried substance of the W/O emulsion (preferably a dried substance of the W/O emulsion) in light of its capability of reducing the number average particle diameter of the obtained particles. A heat treatment temperature is, for example, 30 to 60° C., preferably 35 to 50° C., more preferably 35 to 45° C. A heat treatment time is adjusted appropriately in accordance with the heat treatment temperature. The heat treatment time is, for example, 1 to 30 days, preferably 2 to 15 days, more preferably 3 to 7 days. When the W/O emulsion is heat-treated, the particle according to the present invention can be obtained by drying the heat-treated W/O emulsion as described above after the treatment.

Furthermore, other methods for further reducing the number average particle diameter of the obtained particles include a method of filtering with a filter or the like and a method of centrifugally separating the W/O emulsion containing an active ingredient in an aqueous phase or a dried substance of the W/O emulsion (preferably a dried substance of the W/O emulsion), after dispersing as needed the W/O emulsion containing an active ingredient in an aqueous phase, or the dried substance of the W/O emulsion in a solvent or the like. In the case of filtration with a filter, a pore diameter of the filter is, for example, 1 μm or less, preferably 0.2 μm or less, more preferably 0.1 or less.

The particle according to the present invention may be used as they are. The particle may be dispersed in the base described above or the like, and then the resultant may also be used.

Furthermore, a preparation can be produced by, for example, a liquid coating method with the particle according to the present invention. In the liquid coating method, additive components, such as an absorption enhancer, a thickener, and a gelling agent, are further added as desired, in addition to the particle and base according to the present invention, to a solvent, such as hexane, toluene or ethyl acetate, so that a ratio can be a predetermined ratio, and then the resultant is stirred to prepare a homogeneous solution. A concentration of a solid content in the solution is preferably 10 to 80% by weight, more preferably 20 to 60% by weight.

Then, a release liner (e.g., a siliconized polyester film) can be evenly coated with the solution containing each of the components as described above by a coater such as a knife coater, a comma coater, or a reverse coater, and then dried to form an agent-containing layer. Then, a supporting material can be laminated onto the layer to obtain a preparation. Depending on the kinds of supporting materials, the layer described above can be formed on a supporting material, and then a release liner can be laminated onto the surface of the layer described above.

Furthermore, in other methods, for example, additive components, such as a base, an absorption enhancer, a stabilizer, a thickener, and a gelling agent, are added to the particle according to the present invention as needed, and then the resultant is mixed. Then, the mixture is, for example, stacked on or immersed in, according to the purpose of use, a natural woven member such as gauze or absorbent cotton; a synthetic fiber woven member such as polyester or polyethylene; a woven fabric, a non-woven fabric, or the like made of a desirable combination of the above materials; or a permeable membrane, so that the mixture is retained. Further, the material retaining the mixture can be covered with an adhesive cover material or the like, and the resultant material can also be used.

The thus obtained preparation is cut into a shape of an ellipse, a circle, a square, a rectangle, or the like as needed, according to the purpose of use. Further, an adhesive agent phase or the like may be made on the periphery of the preparation as needed.

EXAMPLES

The present invention will be described, below in detail with reference to examples and test examples, but is not limited to the examples and the test examples.

Example 1

In 40 g of pure water was dissolved 0.1 g of memantine hydrochloride. To the resultant solution was added a solution of 5 g of sucrose laurate (L-195, manufactured by Mitsubishi-Kagaku Foods Corporation, main components are diester and triester) dissolved in 80 g of cyclohexane, and stirred with a homogenizer (10,000 rpm). Then, the mixture was freeze-dried for 2 days to prepare a core-shell structured body (weight ratio of drug:alkyl chain=1:25, approximately). To 11.4 g of isopropyl myristate was added 2.85 g of the resultant product, dispersed by stirring with stirrer, and then filtered with a filter (pore diameter: 0.2 µm, PTFE filter F 2513-4, manufactured by SANPLATEC CORPORATION) to give an external preparation of Example 1. A number average particle diameter calculated by dynamic light scattering (Zetasizer Nano S, manufactured by Spectris Co., Ltd.) was 17 nm.

Example 2

An external preparation was produced (weight ratio of drug:alkyl chain=1:30, approximately) in the same way as in Example 1 except that sucrose erucate (ER-290, manufactured by Mitsubishi-Kagaku Foods Corporation, main components are diester and triester) was used instead of sucrose laurate. A number average particle diameter calculated by dynamic light scattering (manufactured by Spectris Co., Ltd., Zetasizer Kano S) was 12 nm.

Example 3

An external preparation was produced (weight ratio of drug:alkyl chain=1 20, approximately) in the same way as Example 2 except that sucrose erucate was used in an amount of 3 g. A number average particle diameter calculated by dynamic light scattering (Zetasizer Nano S, manufactured by Spectris Co., Ltd.) was 39 nm.

Comparative Example 1

In 40 g of pure water was dissolved 0.1 g of memantine hydrochloride. To the resultant solution was added a solution of 5 g of sucrose laurate (L-195, manufactured by Mitsubishi-Kagaku Foods Corporation, main components are diester and triester) dissolved in 80 g of cyclohexane, and stirred with a homogenizer (10,000 rpm). Then, the mixture was freeze-dried for 2 days to prepare a core-shell structured body (weight ratio of drug:alkyl chain=1:25, approximately). To 11.4 g of isopropyl myristate was added 2.85 g of the resultant product, and then dispersed by stirring with stirrer. To 11.4 g of isopropyl myristate was added a precipitate obtained by centrifugation (12000 rpm) of the dispersion, and then the resultant was dispersed by stirring with stirrer to produce a comparative external preparation. A number average particle diameter calculated by dynamic light scattering (Zetasizer Nano S, manufactured by Spectris Co., Ltd.) was 830 nm.

Comparative Example 2

To 8.3 parts of memantine and 91.7 parts of an acrylic adhesive (Duro-Tak 87-2510) was added ethyl acetate, so that a content of nonvolatile material was 30%, and then the resultant mixture was mixed enough to make the mixture uniform to prepare a liquid paste. The obtained liquid paste was uniformly applied on a release paper, dried at 80° C., then stacked with a supporting material consisting of a polyethylene terephthalate film, and then the resultant was punched, so that the punched material had an area of 3 cm$^2$ to obtain an external preparation for comparison.

Test Example 1 Test of Transdermal Penetration Through Hairless Rat Skin

A hairless rat skin (excised from HWY/Slc aged 8 weeks, Japan SLC, Inc.) was placed in a cell for a test of transdermal drug-penetration (FIG. 1). To the upper part of the apparatus, 2 ml of each of the external preparations produced in Examples 1 to 3 and Comparative Example 1, or the external preparation produced in Comparative Example 2 was applied. A buffer solution adjusted to pH 7.2 with NaOB was poured into a receptor layer at the lower part of the apparatus, wherein the buffer solution contained $5\times10^{-4}$ M $NaH_2PO_4$, $2\times10^{-4}$, $1.5\times10^{-4}$ M Hacl, and 10 ppm of gentamicin sulfate (G1658, manufactured by Wako Pure Chemical Industries, Ltd.) in distilled water. The apparatus was placed in a thermostatic chamber keeping the temperature at 32° C. from the beginning of the test. At a predetermined time after the test was started, 1 ml sample of liquid in the thermostatic chamber was taken from the receptor layer at the lower part of the apparatus, and immediately afterwards 1 ml of liquid having the same composition was refilled. Methanol was added to each of the collected sample liquid to extract an elated lipid or the like, and the resultant was centrifuged. Then, memantine hydrochloride concentration in the supernatant was quantified by GC (column: ZB1, manufactured by JEOL Ltd., length: 30 m, inner diameter: 0.32 mm).

The results are shown in Table 2. In Comparative Examples 1 and 2, an amount of drug penetration was suddenly increased, and the amount of penetration was saturated in a short period of time.

On the contrary, in the external preparations in Examples, sudden increase of drug penetration did not occur. Thus, it was found that the sustained penetration can be maintained.

Test Example 2 Test of Shape Stability

Stability of produced samples for evaluation was confirmed with the use of a shape of a preparation observed by an optical microscope (Model: Eclipse ME 600, manufactured by NIKON CORPORATION) (magnification: 200×) as an index.
The sample was placed at 25° C. (room temperature) for 2 days, and then the shape of the sample was compared to that of the initial state. The following evaluation items were used as indices.
(Items for Shape Evaluation)
○: No change
Δ: Partially changed
×: changed The results of the study for stability of various samples for evaluation are shown in Table 1. A remarkable change of shape was observed in the sample of Comparative Example 1, whereas changes of shapes of the external preparations of Examples were slight. Form these results, it was confirmed that the external preparations of Examples are stable in shape.

TABLE 1

| Sample | Shape change |
|---|---|
| Example 1 | ○ |
| Example 2 | ○ |
| Example 3 | Δ |
| Comparative Example 1 | X |

Example 4

In 40 g of pure water was dissolved 0.1 g of donepezil hydrochloride (manufactured by NACALAI TESQUE, INC.). To the resultant solution was added a solution of 1.5 g of sucrose erucate (ER-290, manufactured by Mitsubishi-Kagaku Foods Corporation; HLB value: 2) dissolved in 80 g of cyclohexane, and stirred with a homogenizer (25,000 rpm). Then, the mixture was freeze-dried for 2 days, and then left still at 40° C. for 5 days to prepare a particle (weight ratio of drug:alkyl chain=1:10). Further, the particle was dispersed in olive squalane (manufactured by Nikko Chemicals Co., Ltd.). A number average particle diameter calculated by dynamic light scattering (Zetasizer Nano S, manufactured by Spectris Co., Ltd. 5 was 9 nm.

Example 5

To 1.5 g of Plastibase® (manufactured by Taisho Pharmaceutical Co., Ltd., Japanese Pharmacopoeia) was added 1.5 g of the particle obtained in Example 4, and then dispersed by mixing to produce an external preparation.

Example 6

A particle was adjusted in the same way as in Example 4 except that sucrose oleate (0-170, manufactured by Mitsubishi-Kagaku Foods Corporation; HLB value: 1) was used instead of sucrose erucate (weight ratio of drug:alkyl chain=1:10). Further, the particle was dispersed in olive squalane. A number average particle diameter calculated by dynamic light scattering (Zetasizer Nano S, manufactured by Spectris Co., Ltd.) was 8 nm.

Example 7

A particle was adjusted in the same way as in Example 4 except that sucrose erucate was used in an amount of 3.0 g (weight ratio of drug:alkyl chain=1:20). Further, the particle was dispersed in olive squalane. A number average particle diameter calculated by dynamic light scattering (Zetasizer Nano S, manufactured by Spectris Co., Ltd.) was 4 nm.

Example 6

A particle was adjusted in the same way as in Example 4 except that vardenafil hydrochloride was used instead of donepezil hydrochloride (weight ratio of drug:alkyl chain=1:10). Further, the particle was dispersed in olive squalane. A number average particle diameter calculated by dynamic light scattering (Zetasizer Nano S, manufactured by Spectris Co., Ltd.) was 12 nm.

Example 9

A particle was adjusted in the same way as in Example 4 except that the freeze-dried mixture was left still at 40° C. for 1 day (weight ratio of drug:alkyl chain=1:10). Further, the particle was dispersed in olive squalane. A number average particle diameter calculated by dynamic light scattering (Zetasizer Nano S, manufactured by Spectris Co., Ltd.) was 46 nm.

Example 10

A particle was adjusted in the same way as in Example 8 except that the freeze-dried mixture was left still at 40° C. for 1 day (weight ratio of drug:alkyl chain=1:10). Further, the particle was dispersed in olive squalane. A number average particle diameter calculated by dynamic light scattering (Zetasizer Nano S, manufactured by Spectris Co., Ltd.) was 82 nm.

Example 11

A particle was adjusted in the same way as in Example 4 except that sucrose erucate was used in an amount of 0.5 g (weight ratio of drug:alkyl chain=1:3.3). Further, the particle was dispersed in olive squalane. A number average particle diameter calculated by dynamic light scattering (Zetasizer Nano S, manufactured by Spectris Co., Ltd.) was 26 nm.

Comparative Example 3

A particle was adjusted in the same way as in Example 4 except that the mixture was not left still at 40° C. for 5 days (weight ratio of drug:alkyl chain=1:10). further, the particle was dispersed in olive squalane. A number average particle diameter calculated by dynamic light scattering (Zetasizer Nano S, manufactured by Spectris Co., Ltd.) was 210 nm.

Comparative Example 4

An external preparation was prepared in the same way as in Example 5 except that the particle obtained in Comparative Example 3 were used.

Comparative Example 5

A particle was adjusted in the same way as in Example 7 except that the mixture was not left still at 40° C. for 5 days (weight ratio of drug:alkyl chain=1:20). Further, the particle was dispersed in olive squalane. A number average particle diameter calculated by dynamic light scattering (Zetasizer Nano S, manufactured by Spectris Co., Ltd.) was 280 nm.

Comparative Example 6

A particle was adjusted in the same way as in Example 8 except that the mixture was not left still at 40° C. for 5 days (weight ratio of drug:alkyl chain=1:10). Further, the particle was dispersed in olive squalane. A number average particle diameter calculated by dynamic light scattering (Zetasizer Kano 8, manufactured by Spectris Co., Ltd.) was 350 nm.

Comparative Example 7

To 1.5 g of Plastibase® was added 0.094 g of donepezil hydrochloride, and then dispersed by mixing to produce an external preparation.

Test Example 3 Test of Durability

The particle of Examples 4 and 6 to 11, and Comparative Examples of 3 and 5 to 6 was dispersed at a concentration of 30% by weight in ethyl acetate (manufactured by Wako Pure Chemical Industries, Ltd.), and then the solvent was removed at 60° C. Then, the resultant particle was dispersed in olive squalane. Change of each particle in appearance from that of at the time of dispersing the particle of Examples 4 and 6 to 11, and Comparative Examples of 3 and 5 to 6 in olive squalane was visually observed.
The following evaluation items were used as indices.
(Items for Shape Evaluation)
○: No change
Δ: Partially changed
×: Changed
The results of the study for durability of various samples for evaluation are shown in Table 2. Remarkable changes in appearance were observed in the particle of Comparative Examples (presumed due to particle disintegration), whereas changes in appearance of the particle of Examples were slight.

TABLE 2

| Sample | Change in appearance |
|---|---|
| Example 4 | ○ |
| Example 6 | ○ |
| Example 7 | ○ |
| Example 8 | ○ |
| Example 9 | Δ |
| Example 10 | Δ |
| Example 11 | Δ |
| Comparative Example 3 | X |
| Comparative Example 5 | X |
| Comparative Example 6 | X |

Test Example 4 Test, of Transdermal Penetration Through Hairless Rat Skin

A hairless rat skin (excised from HWY/Slc aged 8 weeks, Japan SLC, Inc.) was placed in a cell for a test of transdermal drug-penetration (FIG. 1). To the upper part of the apparatus, 0.5 g (about 3 cm$^2$) of each of the external preparations produced in Example 5 and Comparative Examples 4 and 7 was applied. A buffer solution adjusted to pH 7.2 with NaOH was poured into a receptor layer at the lower part of the apparatus, wherein the buffer solution contained 5×10$^{-4}$ M NaH$_2$PO$_4$, 2×10$^{-4}$ M Na$_2$HPO$_4$, 1.5∴10$^{-4}$ M NaCl, and 10 ppm of gentamicin sulfate (G1658, manufactured by Wako Pure Chemical Industries, Ltd.) in distilled water. The apparatus was placed in a thermostatic chamber keeping the temperature at 32° C. from the beginning of the test. At a predetermined time after the test was started, 1 ml sample of liquid in the thermostatic chamber was taken from the receptor layer at the lower part of the apparatus, and immediately afterwards 1 ml of liquid having the same composition was refilled. Methanol was added to each of the collected sample receptor liquid to extract an eluted lipid or the like, and the resultant was centrifuged. Then, donepezil hydrochloride concentration in the the supernatant was quantified by high-performance liquid chromatography (HPLC) (System: System controller: CBM-20A, manufactured by SHIMADZU CORPORATION; Solvent delivery unit: LC-20AD, manufactured by SHIMADZU CORPORATION; Column oven: CTO-20A, manufactured by SHIMADZU CORPORATION; Detector: SPD-20A, manufactured by SHIMADZU CORPORATION; Detection wavelength: 271 nm; Column used: Hypersi GOLD 150×4.6 mm 3 μm, manufactured by Thermo Scientific, Mobile phase: 0.15% perchloric acid aqueous solution/acetonitrile=1300/700, Column temperature: 35° C., Flow rate: 1.25 ml/min).

The results are shown in Table 3. It was found that the external preparation of Example 5 shows higher amount of sustained drug penetration as compared to that of the external preparation of Comparative Example 7, and shows the same or higher amount of sustained drug penetration as compared to that of Comparative Example 4.

Form these results, it was confirmed that the particle of Examples exerts large amount of transdermal penetration, and that the particle is stable and highly durable.

DESCRIPTION OF REFERENCE SYMBOLS

1 . . . Parafilm
2 . . . Skin
3 . . . Preparation
4 . . . Receptor liquid (Phosphate buffer, pF=7.2)
5 . . . Stirring bar

The invention claimed is:

1. A method for producing a storage stable particle comprising a storage stable first fraction containing a hydrophilic active ingredient and a second fraction containing a surfactant having a weighted average of HLB value of 10 or less, wherein a portion of a surface of or a whole surface of the first fraction is coated with the second fraction, and the particle is a core-shell structured body in which the first fraction corresponds to a core portion and the second fraction corresponds to a shell portion, the method comprising:
   a step of freeze-drying or vacuum-drying a W/O emulsion containing the active ingredient in, an aqueous phase,
   a step of heat-treating a dried substance of the W/O emulsion, and
   a step of obtaining a particle having a number average particle diameter of from 1 to 12 nm by heat-treating a dried substance of the W/O emulsion containing an active ingredient in an aqueous phase.

2. The method for production according to claim 1, wherein the particle has a water content of 20% by weight or less.

3. The method for production according to claim 1, wherein, in the heat-treating step, the heat treatment temperature is 30° C. to 60° C.

4. The method for production according to claim 1, wherein, in the heat-treating step, the heat treatment time is 1 day to 30 days.

* * * * *